(12) United States Patent
Whitman

(10) Patent No.: US 9,782,172 B2
(45) Date of Patent: *Oct. 10, 2017

(54) ELECTROMECHANICAL DRIVE AND REMOTE SURGICAL INSTRUMENT ATTACHMENT HAVING COMPUTER ASSISTED CONTROL CAPABILITIES

(71) Applicant: Covidien LP, Mansfield, MA (US)

(72) Inventor: Michael P. Whitman, New Hope, PA (US)

(73) Assignee: Covidien LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/992,205

(22) Filed: Jan. 11, 2016

(65) Prior Publication Data

US 2016/0120539 A1    May 5, 2016

Related U.S. Application Data

(60) Continuation of application No. 14/678,043, filed on Apr. 3, 2015, which is a continuation of application
(Continued)

(51) Int. Cl.
*A61B 17/068* (2006.01)
*A61B 17/115* (2006.01)
(Continued)

(52) U.S. Cl.
CPC .......... *A61B 17/068* (2013.01); *A61B 5/6885* (2013.01); *A61B 17/07207* (2013.01);
(Continued)

(58) Field of Classification Search
CPC .......... A61B 17/07207; A61B 17/1114; A61B 17/115; A61B 17/1155; A61B 17/086;
(Continued)

(56) References Cited

U.S. PATENT DOCUMENTS 1,798,902 A   3/1931 Raney
1,881,250 A   10/1932 Tomlinson
(Continued)

FOREIGN PATENT DOCUMENTS

DE   2903159 A1   7/1980
DE   3114135 A1   10/1982
(Continued)

OTHER PUBLICATIONS

Japanese Office Action for application No. 2015-170009 dated Jun. 24, 2016.
(Continued)

*Primary Examiner* — Pedro Philogene

(57) ABSTRACT

A medical tool comprising an electromechanical driver and a surgical instrument attachment for use in invasive surgery, including a handle coupled to a flexible sheath which is in turn coupled to a surgical attachment. The handle of the driver includes the electromechanical driver and at least one processor element which controls the actions of the electromechanical driver, and therefore the application elements of the surgical attachment, based on information relayed between the processor element and remotely activatable sensor assemblies in the surgical instrument attachment.

20 Claims, 4 Drawing Sheets

Related U.S. Application Data

No. 14/192,014, filed on Feb. 27, 2014, now Pat. No. 9,241,716, which is a continuation of application No. 13/191,893, filed on Jul. 27, 2011, now Pat. No. 8,690,913, which is a continuation of application No. 12/838,706, filed on Jul. 19, 2010, now Pat. No. 8,016,858, which is a continuation of application No. 11/488,369, filed on Jul. 17, 2006, now Pat. No. 7,758,613, which is a continuation of application No. 10/761,491, filed on Jan. 20, 2004, now Pat. No. 7,077,856, which is a division of application No. 09/510,927, filed on Feb. 22, 2000, now Pat. No. 6,716,233, which is a continuation-in-part of application No. 09/324,452, filed on Jun. 2, 1999, now Pat. No. 6,443,973.

(51) Int. Cl.
  *A61B 5/00* (2006.01)
  *A61B 17/072* (2006.01)
  *A61B 17/11* (2006.01)
  *A61B 5/1459* (2006.01)
  *A61B 17/00* (2006.01)
  *A61B 17/29* (2006.01)

(52) U.S. Cl.
  CPC ......... *A61B 17/115* (2013.01); *A61B 17/1114* (2013.01); *A61B 17/1152* (2013.01); *A61B 17/1155* (2013.01); *A61B 5/1459* (2013.01); *A61B 2017/00022* (2013.01); *A61B 2017/00039* (2013.01); *A61B 2017/00292* (2013.01); *A61B 2017/00367* (2013.01); *A61B 2017/00398* (2013.01); *A61B 2017/00464* (2013.01); *A61B 2017/00473* (2013.01); *A61B 2017/00734* (2013.01); *A61B 2017/07214* (2013.01); *A61B 2017/07278* (2013.01); *A61B 2017/2905* (2013.01)

(58) Field of Classification Search
  CPC . A61B 17/1152; A61B 5/6885; A61B 5/1459; A61B 2017/00367; A61B 2017/00022; A61B 2017/00039; A61B 2017/00292; A61B 2017/00398; A61B 2017/00464; A61B 2017/00473; A61B 2017/00734; A61B 2017/07214; A61B 2017/07278; A61B 2017/2905
  USPC ......... 227/175.1, 5, 19, 176.1, 178.1, 180.1; 606/219, 170, 171, 167, 75
  See application file for complete search history.

(56) References Cited

U.S. PATENT DOCUMENTS

| | | |
|---|---|---|
| 2,031,682 A | 2/1936 | Wappler et al. |
| 2,174,219 A | 9/1939 | Balma |
| 2,246,647 A | 6/1941 | Vancura |
| 2,419,045 A | 4/1947 | Whittaker |
| 2,725,628 A | 12/1955 | O'Neilly et al. |
| 3,079,606 A | 3/1963 | Bobrov et al. |
| 3,120,845 A | 2/1964 | Horner |
| 3,193,165 A | 7/1965 | Akhalaya et al. |
| 3,252,643 A | 5/1966 | Strekopov et al. |
| 3,256,875 A | 6/1966 | Tsepelev et al. |
| 3,275,211 A | 9/1966 | Hirsch et al. |
| 3,315,863 A | 4/1967 | O'Dea |
| 3,317,105 A | 5/1967 | Astafjev et al. |
| 3,388,847 A | 6/1968 | Kasulin et al. |
| 3,490,576 A | 1/1970 | Alessi et al. |
| 3,490,675 A | 1/1970 | Green et al. |
| 3,494,533 A | 2/1970 | Green et al. |
| 3,499,591 A | 3/1970 | Green |
| 3,552,626 A | 1/1971 | Astafiev et al. |
| 3,568,659 A | 3/1971 | Karnegis |
| 3,589,589 A | 6/1971 | Akopov |
| 3,593,903 A | 7/1971 | Astafiev et al. |
| 3,618,842 A | 11/1971 | Bryan |
| 3,638,652 A | 2/1972 | Kelley |
| 3,643,851 A | 2/1972 | Green et al. |
| 3,662,939 A | 5/1972 | Bryan |
| 3,675,688 A | 7/1972 | Bryan et al. |
| 3,692,224 A | 9/1972 | Astafiev et al. |
| 3,717,294 A | 2/1973 | Green |
| 3,735,762 A | 5/1973 | Bryan et al. |
| 3,777,538 A | 12/1973 | Weatherly et al. |
| 3,788,303 A | 1/1974 | Hall |
| 3,795,034 A | 3/1974 | Strekopytov et al. |
| 3,815,476 A | 6/1974 | Green et al. |
| 3,819,100 A | 6/1974 | Noiles et al. |
| 3,837,555 A | 9/1974 | Green |
| 3,844,289 A | 10/1974 | Noiles |
| 3,858,577 A | 1/1975 | Bass et al. |
| 3,859,986 A | 1/1975 | Okada et al. |
| 3,882,854 A | 5/1975 | Hulka et al. |
| 3,892,228 A | 7/1975 | Mitsui |
| 3,935,981 A | 2/1976 | Akopov et al. |
| 3,949,924 A | 4/1976 | Green |
| 3,952,748 A | 4/1976 | Kaliher et al. |
| RE28,932 E | 8/1976 | Noiles et al. |
| 4,014,492 A | 3/1977 | Rothfuss |
| 4,027,510 A | 6/1977 | Hiltebrandt |
| 4,060,089 A | 11/1977 | Noiles |
| 4,064,881 A | 12/1977 | Meredith |
| 4,071,029 A | 1/1978 | Richmond et al. |
| 4,085,756 A | 4/1978 | Weaver |
| 4,086,926 A | 5/1978 | Green et al. |
| 4,092,986 A | 6/1978 | Schneiderman |
| 4,111,206 A | 9/1978 | Vishnevsky et al. |
| 4,169,476 A | 10/1979 | Hiltebrandt |
| 4,198,960 A | 4/1980 | Utsugi |
| 4,198,982 A | 4/1980 | Fortner et al. |
| 4,202,479 A | 5/1980 | Razgulov et al. |
| 4,202,480 A | 5/1980 | Annett |
| 4,207,873 A | 6/1980 | Kruy |
| 4,207,898 A | 6/1980 | Becht |
| 4,244,372 A | 1/1981 | Kapitanov et al. |
| 4,250,873 A | 2/1981 | Bonnet |
| 4,261,244 A | 4/1981 | Becht et al. |
| 4,273,109 A | 6/1981 | Enderby |
| 4,273,111 A | 6/1981 | Tsukaya |
| 4,273,129 A | 6/1981 | Boebel |
| 4,286,585 A | 9/1981 | Ogawa |
| 4,289,131 A | 9/1981 | Mueller |
| 4,289,133 A | 9/1981 | Rothfuss |
| 4,296,881 A | 10/1981 | Lee |
| 4,304,236 A | 12/1981 | Conta et al. |
| 4,310,115 A | 1/1982 | Inoue |
| 4,319,576 A | 3/1982 | Rothfuss |
| 4,325,377 A | 4/1982 | Boebel |
| 4,334,539 A | 6/1982 | Childs et al. |
| 4,349,028 A | 9/1982 | Green |
| 4,351,466 A | 9/1982 | Noiles |
| 4,354,628 A | 10/1982 | Green |
| 4,367,729 A | 1/1983 | Ogiu |
| 4,379,457 A | 4/1983 | Gravener et al. |
| 4,383,634 A | 5/1983 | Green |
| 4,391,401 A | 7/1983 | Moshofsky |
| 4,402,311 A | 9/1983 | Hattori |
| 4,402,445 A | 9/1983 | Green |
| 4,429,695 A | 2/1984 | Green |
| 4,442,964 A | 4/1984 | Becht |
| 4,445,509 A | 5/1984 | Auth |
| 4,445,892 A | 5/1984 | Hussein et al. |
| 4,448,188 A | 5/1984 | Loeb |
| 4,461,305 A | 7/1984 | Cibley |
| 4,473,077 A | 9/1984 | Noiles et al. |
| 4,476,863 A | 10/1984 | Kanshin et al. |
| 4,485,817 A | 12/1984 | Swiggett |
| 4,487,270 A | 12/1984 | Huber |
| 4,488,523 A | 12/1984 | Shichman |

(56) References Cited

U.S. PATENT DOCUMENTS

| | | |
|---|---|---|
| 4,489,724 A | 12/1984 | Arnegger |
| 4,489,875 A | 12/1984 | Crawford et al. |
| 4,494,057 A | 1/1985 | Hotta |
| 4,494,549 A | 1/1985 | Namba et al. |
| 4,499,895 A | 2/1985 | Takayama |
| 4,505,272 A | 3/1985 | Utyamyshev et al. |
| 4,505,414 A | 3/1985 | Filipi |
| 4,506,670 A | 3/1985 | Crossley |
| 4,506,671 A | 3/1985 | Green |
| 4,513,746 A | 4/1985 | Aranyi et al. |
| 4,519,532 A | 5/1985 | Foslien |
| 4,520,817 A | 6/1985 | Green |
| 4,527,724 A | 7/1985 | Chow et al. |
| 4,534,352 A | 8/1985 | Korthoff |
| 4,534,420 A | 8/1985 | Goldelius |
| 4,559,928 A | 12/1985 | Takayama |
| 4,566,620 A | 1/1986 | Green et al. |
| 4,573,468 A | 3/1986 | Conta et al. |
| 4,573,622 A | 3/1986 | Green et al. |
| 4,574,806 A | 3/1986 | McCarthy |
| 4,576,167 A | 3/1986 | Noiles |
| 4,589,412 A | 5/1986 | Kensey |
| 4,589,416 A | 5/1986 | Green |
| 4,589,582 A | 5/1986 | Bilotti |
| 4,591,085 A | 5/1986 | Di Giovanni |
| 4,592,354 A | 6/1986 | Rothfuss |
| 4,593,679 A | 6/1986 | Collins |
| 4,603,693 A | 8/1986 | Conta et al. |
| 4,605,001 A | 8/1986 | Rothfuss et al. |
| 4,606,343 A | 8/1986 | Conta et al. |
| 4,607,638 A | 8/1986 | Crainich |
| 4,610,383 A | 9/1986 | Rothfuss et al. |
| 4,631,052 A | 12/1986 | Kensey |
| 4,633,861 A | 1/1987 | Chow et al. |
| 4,633,874 A | 1/1987 | Chow et al. |
| 4,643,190 A | 2/1987 | Heimberger |
| 4,644,952 A | 2/1987 | Patipa et al. |
| 4,646,745 A | 3/1987 | Noiles |
| 4,655,673 A | 4/1987 | Hawkes |
| 4,657,017 A | 4/1987 | Sorochenko |
| 4,664,305 A | 5/1987 | Blake, III et al. |
| 4,667,673 A | 5/1987 | Li |
| 4,669,471 A | 6/1987 | Hayashi |
| 4,671,445 A | 6/1987 | Barker et al. |
| 4,672,961 A | 6/1987 | Davies |
| 4,674,515 A | 6/1987 | Andou et al. |
| 4,688,555 A | 8/1987 | Wardle |
| 4,696,667 A | 9/1987 | Masch |
| 4,700,703 A | 10/1987 | Resnick et al. |
| 4,703,887 A | 11/1987 | Clanton et al. |
| 4,705,038 A | 11/1987 | Sjostrom et al. |
| 4,708,141 A | 11/1987 | Inoue et al. |
| 4,714,187 A | 12/1987 | Green |
| 4,715,502 A | 12/1987 | Salmon |
| 4,728,020 A | 3/1988 | Green et al. |
| 4,732,156 A | 3/1988 | Nakamura |
| 4,733,118 A | 3/1988 | Mihalko |
| 4,742,815 A | 5/1988 | Ninan et al. |
| 4,752,024 A | 6/1988 | Green et al. |
| 4,754,909 A | 7/1988 | Barker et al. |
| 4,756,309 A | 7/1988 | Sachse et al. |
| 4,760,840 A | 8/1988 | Fournier, Jr. et al. |
| 4,763,669 A | 8/1988 | Jaeger |
| 4,767,044 A | 8/1988 | Green |
| 4,771,774 A | 9/1988 | Simpson et al. |
| 4,776,506 A | 10/1988 | Green |
| 4,781,186 A | 11/1988 | Simpson et al. |
| 4,784,137 A | 11/1988 | Kulik et al. |
| 4,805,823 A | 2/1989 | Rothfuss |
| 4,815,469 A | 3/1989 | Cohen et al. |
| 4,817,847 A | 4/1989 | Redtenbacher et al. |
| 4,819,632 A | 4/1989 | Davies |
| 4,819,853 A | 4/1989 | Green |
| 4,841,888 A | 6/1989 | Mills et al. |
| 4,848,637 A | 7/1989 | Pruitt |
| 4,858,608 A | 8/1989 | McQuilkin |
| 4,863,088 A | 9/1989 | Redmond et al. |
| 4,867,158 A | 9/1989 | Sugg |
| 4,873,977 A | 10/1989 | Avant et al. |
| 4,887,599 A | 12/1989 | Muller |
| 4,887,612 A | 12/1989 | Esser et al. |
| 4,890,602 A | 1/1990 | Hake |
| 4,892,244 A | 1/1990 | Fox et al. |
| 4,893,613 A | 1/1990 | Hake |
| 4,893,622 A | 1/1990 | Green et al. |
| 4,903,697 A | 2/1990 | Resnick et al. |
| 4,907,591 A | 3/1990 | Vasconcellos et al. |
| 4,907,973 A | 3/1990 | Hon |
| 4,917,114 A | 4/1990 | Green et al. |
| 4,919,152 A | 4/1990 | Ger |
| 4,928,699 A | 5/1990 | Sasai |
| 4,930,494 A | 6/1990 | Takehana et al. |
| 4,932,960 A | 6/1990 | Green et al. |
| 4,936,845 A | 6/1990 | Stevens |
| 4,941,623 A | 7/1990 | Pruitt |
| 4,944,093 A | 7/1990 | Falk |
| 4,944,443 A | 7/1990 | Oddsen et al. |
| 4,955,882 A | 9/1990 | Hakky |
| 4,955,959 A | 9/1990 | Tompkins et al. |
| 4,957,499 A | 9/1990 | Lipatov et al. |
| 4,962,877 A | 10/1990 | Hervas |
| 4,976,688 A | 12/1990 | Rosenblum |
| 4,976,710 A | 12/1990 | Mackin |
| 4,977,900 A | 12/1990 | Fehling et al. |
| 4,978,049 A | 12/1990 | Green |
| 4,982,726 A | 1/1991 | Taira |
| 4,991,764 A | 2/1991 | Mericle |
| 4,994,060 A | 2/1991 | Rink et al. |
| 4,995,877 A | 2/1991 | Ams et al. |
| 5,005,749 A | 4/1991 | Aranyi |
| 5,018,657 A | 5/1991 | Pedlick et al. |
| 5,031,814 A | 7/1991 | Tompkins et al. |
| 5,040,715 A | 8/1991 | Green et al. |
| 5,059,203 A | 10/1991 | Husted |
| 5,071,430 A | 12/1991 | de Salis et al. |
| 5,077,506 A | 12/1991 | Krause |
| 5,104,025 A | 4/1992 | Main et al. |
| 5,108,391 A | 4/1992 | Flachenecker et al. |
| 5,119,983 A | 6/1992 | Green et al. |
| 5,133,359 A | 7/1992 | Kedem |
| 5,133,713 A | 7/1992 | Huang et al. |
| 5,133,729 A | 7/1992 | Sjostrom |
| 5,139,513 A | 8/1992 | Segato |
| 5,156,315 A | 10/1992 | Green et al. |
| 5,157,837 A | 10/1992 | Rose |
| 5,158,222 A | 10/1992 | Green et al. |
| 5,170,925 A | 12/1992 | Madden et al. |
| 5,171,247 A | 12/1992 | Hughett et al. |
| 5,171,251 A | 12/1992 | Bregen et al. |
| 5,173,133 A | 12/1992 | Morin et al. |
| 5,192,292 A | 3/1993 | Cezana et al. |
| 5,197,649 A | 3/1993 | Bessler et al. |
| 5,201,325 A | 4/1993 | McEwen et al. |
| 5,201,750 A | 4/1993 | Hocherl et al. |
| 5,205,459 A | 4/1993 | Brinkerhoff et al. |
| 5,207,691 A | 5/1993 | Nardella |
| 5,207,697 A | 5/1993 | Carusillo et al. |
| 5,217,460 A | 6/1993 | Knoepfler |
| 5,237,884 A | 8/1993 | Seto |
| 5,249,583 A | 10/1993 | Mallaby |
| 5,253,793 A | 10/1993 | Green et al. |
| 5,254,117 A | 10/1993 | Rigby et al. |
| 5,258,004 A | 11/1993 | Bales et al. |
| 5,258,007 A | 11/1993 | Spetzler et al. |
| 5,258,008 A | 11/1993 | Wilk |
| 5,261,877 A | 11/1993 | Fine et al. |
| 5,267,997 A | 12/1993 | Farin et al. |
| 5,268,622 A | 12/1993 | Philipp |
| 5,271,543 A | 12/1993 | Grant et al. |
| 5,271,544 A | 12/1993 | Fox et al. |
| 5,275,322 A | 1/1994 | Brinkerhoff et al. |
| 5,275,609 A | 1/1994 | Pingleton et al. |
| 5,279,565 A | 1/1994 | Klein et al. |
| 5,285,945 A | 2/1994 | Brinkerhoff et al. |

(56) References Cited

U.S. PATENT DOCUMENTS

| | | |
|---|---|---|
| 5,289,963 A | 3/1994 | McGarry et al. |
| 5,290,299 A | 3/1994 | Fain et al. |
| 5,290,303 A | 3/1994 | Pingleton et al. |
| 5,292,053 A | 3/1994 | Bilotti et al. |
| 5,295,990 A | 3/1994 | Levin |
| 5,300,087 A | 4/1994 | Knoepfler |
| 5,312,023 A | 5/1994 | Green et al. |
| 5,312,434 A | 5/1994 | Crainich |
| 5,318,221 A | 6/1994 | Green et al. |
| 5,320,627 A | 6/1994 | Sorensen et al. |
| 5,322,055 A | 6/1994 | Davison et al. |
| 5,324,288 A | 6/1994 | Billings et al. |
| 5,324,300 A | 6/1994 | Elias et al. |
| 5,326,013 A | 7/1994 | Green et al. |
| 5,330,471 A | 7/1994 | Eggers |
| 5,330,486 A | 7/1994 | Wilk |
| 5,333,773 A | 8/1994 | Main et al. |
| 5,336,229 A | 8/1994 | Noda |
| 5,342,299 A | 8/1994 | Snoke et al. |
| 5,342,381 A | 8/1994 | Tidemand |
| 5,350,104 A | 9/1994 | Main et al. |
| 5,352,222 A | 10/1994 | Rydell |
| 5,352,223 A | 10/1994 | McBrayer et al. |
| 5,352,235 A | 10/1994 | Koros et al. |
| 5,354,266 A | 10/1994 | Snoke |
| 5,356,408 A | 10/1994 | Rydell |
| 5,364,409 A | 11/1994 | Kuwabara et al. |
| 5,366,133 A | 11/1994 | Geiste |
| 5,366,476 A | 11/1994 | Noda |
| 5,368,015 A | 11/1994 | Wilk |
| 5,383,880 A | 1/1995 | Hooven |
| 5,391,156 A | 2/1995 | Hildwein et al. |
| 5,395,030 A | 3/1995 | Kuramoto et al. |
| 5,395,033 A | 3/1995 | Byrne et al. |
| 5,395,369 A | 3/1995 | McBrayer et al. |
| 5,396,900 A | 3/1995 | Slater et al. |
| 5,397,046 A | 3/1995 | Savage et al. |
| D357,535 S | 4/1995 | Grant et al. |
| 5,403,312 A | 4/1995 | Yates et al. |
| 5,403,327 A | 4/1995 | Thornton et al. |
| 5,411,508 A | 5/1995 | Bessler et al. |
| 5,413,267 A | 5/1995 | Solyntjes et al. |
| 5,425,705 A | 6/1995 | Evard et al. |
| 5,425,738 A | 6/1995 | Gustafson et al. |
| 5,425,745 A | 6/1995 | Green et al. |
| 5,433,721 A | 7/1995 | Hooven et al. |
| 5,437,636 A | 8/1995 | Snoke et al. |
| 5,441,507 A | 8/1995 | Wilk |
| 5,456,684 A | 10/1995 | Schmidt et al. |
| 5,460,182 A | 10/1995 | Goodman et al. |
| 5,464,404 A | 11/1995 | Abela et al. |
| 5,465,894 A | 11/1995 | Clark et al. |
| 5,467,911 A | 11/1995 | Tsuruta et al. |
| 5,476,206 A | 12/1995 | Green et al. |
| 5,482,054 A | 1/1996 | Slater et al. |
| 5,482,197 A | 1/1996 | Green et al. |
| 5,485,947 A | 1/1996 | Olson et al. |
| 5,496,269 A | 3/1996 | Snoke |
| 5,496,317 A | 3/1996 | Goble et al. |
| 5,514,134 A | 5/1996 | Rydell et al. |
| 5,518,163 A * | 5/1996 | Hooven ............ A61B 17/07207 227/175.1 |
| 5,518,164 A | 5/1996 | Hooven |
| 5,520,634 A | 5/1996 | Fox et al. |
| 5,524,180 A | 6/1996 | Wang et al. |
| 5,527,313 A | 6/1996 | Scott et al. |
| 5,531,687 A | 7/1996 | Snoke et al. |
| 5,533,661 A | 7/1996 | Main et al. |
| 5,535,937 A | 7/1996 | Boiarski et al. |
| 5,562,677 A | 10/1996 | Hildwein et al. |
| 5,562,702 A | 10/1996 | Huitema et al. |
| 5,569,274 A | 10/1996 | Rapacki et al. |
| 5,578,052 A | 11/1996 | Koros et al. |
| 5,580,067 A | 12/1996 | Hamblin et al. |
| 5,582,611 A | 12/1996 | Tsuruta et al. |
| 5,599,347 A | 2/1997 | Hart et al. |
| 5,603,443 A | 2/1997 | Clark et al. |
| 5,607,094 A | 3/1997 | Clark et al. |
| 5,609,285 A | 3/1997 | Grant et al. |
| 5,618,303 A | 4/1997 | Marlow et al. |
| 5,618,307 A | 4/1997 | Donlon et al. |
| 5,626,607 A | 5/1997 | Malecki et al. |
| 5,653,374 A | 8/1997 | Young et al. |
| 5,662,673 A | 9/1997 | Kieturakis |
| 5,665,100 A | 9/1997 | Yoon |
| 5,667,517 A * | 9/1997 | Hooven ................ A61B 34/76 227/175.1 |
| 5,667,526 A | 9/1997 | Levin |
| 5,688,269 A | 11/1997 | Newton et al. |
| 5,693,042 A | 12/1997 | Boiarski et al. |
| 5,732,871 A | 3/1998 | Clark et al. |
| 5,735,848 A | 4/1998 | Yates et al. |
| 5,735,849 A | 4/1998 | Baden et al. |
| 5,735,861 A | 4/1998 | Peifer et al. |
| 5,741,285 A | 4/1998 | McBrayer et al. |
| 5,749,893 A | 5/1998 | Vidal et al. |
| 5,772,597 A | 6/1998 | Goldberger et al. |
| 5,779,130 A | 7/1998 | Alesi et al. |
| 5,782,396 A | 7/1998 | Mastri et al. |
| 5,797,835 A | 8/1998 | Green |
| 5,797,944 A | 8/1998 | Nobles et al. |
| 5,823,956 A | 10/1998 | Roth et al. |
| 5,846,221 A | 12/1998 | Snoke et al. |
| 5,855,590 A | 1/1999 | Malecki et al. |
| 5,857,996 A | 1/1999 | Snoke |
| 5,860,953 A | 1/1999 | Snoke et al. |
| 5,868,760 A | 2/1999 | McGuckin, Jr. |
| 5,893,875 A | 4/1999 | O'Connor et al. |
| 5,913,842 A | 6/1999 | Boyd et al. |
| 5,915,616 A | 6/1999 | Viola et al. |
| 5,925,055 A | 7/1999 | Adrian et al. |
| 5,954,259 A | 9/1999 | Viola et al. |
| 5,976,156 A | 11/1999 | Taylor et al. |
| 5,984,919 A | 11/1999 | Hilal et al. |
| 5,989,274 A | 11/1999 | Davison et al. |
| 5,993,378 A | 11/1999 | Lemelson |
| 6,007,531 A | 12/1999 | Snoke et al. |
| 6,010,493 A | 1/2000 | Snoke |
| 6,017,322 A | 1/2000 | Snoke et al. |
| 6,059,719 A | 5/2000 | Yamamoto et al. |
| 6,074,402 A | 6/2000 | Peifer et al. |
| 6,086,600 A | 7/2000 | Kortenbach |
| 6,099,466 A * | 8/2000 | Sano ................ A61B 1/00186 600/109 |
| 6,110,188 A | 8/2000 | Narciso, Jr. |
| 6,119,913 A * | 9/2000 | Adams ................ A61B 17/115 227/176.1 |
| 6,126,058 A | 10/2000 | Adams et al. |
| 6,126,591 A | 10/2000 | McGarry et al. |
| 6,368,340 B2 | 4/2002 | Malecki et al. |
| 6,443,973 B1 * | 9/2002 | Whitman .......... A61B 17/07207 227/176.1 |
| 6,517,565 B1 | 2/2003 | Whitman et al. |
| 6,716,233 B1 * | 4/2004 | Whitman .......... A61B 17/07207 606/219 |
| 6,770,081 B1 | 8/2004 | Cooper et al. |
| 7,077,856 B2 * | 7/2006 | Whitman .......... A61B 17/07207 606/219 |
| 7,758,613 B2 * | 7/2010 | Whitman .............. A61B 5/6885 606/219 |
| 8,690,913 B2 * | 4/2014 | Whitman ............. A61B 5/6885 227/175.1 |
| 9,241,716 B2 * | 1/2016 | Whitman .............. A61B 5/6885 |
| 2001/0016750 A1 | 8/2001 | Malecki et al. |
| 2001/0031975 A1 | 10/2001 | Whitman et al. |

FOREIGN PATENT DOCUMENTS

| | | |
|---|---|---|
| DE | 3300768 A1 | 7/1984 |
| DE | 4213426 A1 | 10/1992 |
| EP | 0041022 A1 | 12/1981 |
| EP | 0116220 A1 | 8/1984 |
| EP | 0121474 A2 | 10/1984 |

(56) References Cited

FOREIGN PATENT DOCUMENTS

| | | |
|---|---|---|
| EP | 0156774 A2 | 10/1985 |
| EP | 0216532 A1 | 4/1987 |
| EP | 0293123 A2 | 11/1988 |
| EP | 0 324 166 A2 | 7/1989 |
| EP | 0324637 A1 | 7/1989 |
| EP | 0365153 A1 | 4/1990 |
| EP | 0369324 A1 | 5/1990 |
| EP | 0373762 A1 | 6/1990 |
| EP | 0399701 A1 | 11/1990 |
| EP | 0484677 A1 | 5/1992 |
| EP | 0514139 A2 | 11/1992 |
| EP | 0536903 A2 | 4/1993 |
| EP | 0539762 A1 | 5/1993 |
| EP | 0552050 A2 | 7/1993 |
| EP | 0552423 A2 | 7/1993 |
| EP | 0581400 A1 | 2/1994 |
| EP | 0593920 A1 | 4/1994 |
| EP | 0598579 A1 | 5/1994 |
| EP | 0621006 A1 | 10/1994 |
| EP | 0630612 A1 | 12/1994 |
| EP | 0639349 A2 | 2/1995 |
| EP | 0679367 A2 | 11/1995 |
| GB | 1352554 A | 5/1974 |
| GB | 1452185 A | 10/1976 |
| GB | 2038692 A | 7/1980 |
| GB | 2044108 A | 10/1980 |
| GB | 2048685 A | 12/1980 |
| GB | 2165559 A | 4/1986 |
| GB | 2180455 A | 4/1987 |
| JP | H067357 A | 1/1994 |
| JP | 05337119 B2 | 11/2013 |
| JP | 05337121 B2 | 11/2013 |
| NL | 7711347 A | 4/1979 |
| SU | 659146 | 4/1979 |
| WO | 8300992 A1 | 3/1983 |
| WO | 9005491 A2 | 5/1990 |
| WO | 9006085 A1 | 6/1990 |
| WO | 9216141 A1 | 10/1992 |
| WO | 9308754 A1 | 5/1993 |
| WO | 9314706 A1 | 8/1993 |
| WO | 9747231 A2 | 12/1997 |
| WO | 0072765 A1 | 12/2000 |

OTHER PUBLICATIONS

Japanese Publication No. 10-305042; A machine language translation of the abstract is as follows: "A cervical extension apparatus which has a removableattachement 20."

Extended European Search Report corresponding to EP 10 01 0187.2, completed Feb. 26, 2014 and mailed Mar. 14, 2014; (5 pp).

European Office Action for EP Appln. No. 10 010 027.0 dated Apr. 30, 2015.

* cited by examiner

ELECTROMECHANICAL DRIVE AND REMOTE SURGICAL INSTRUMENT ATTACHMENT HAVING COMPUTER ASSISTED CONTROL CAPABILITIES

CROSS-REFERENCE TO RELATED APPLICATIONS

This application is a continuation claiming the benefit of and priority to U.S. patent application Ser. No. 14/678,043, filed Apr. 3, 2015, which is a continuation claiming the benefit of and priority to U.S. patent application Ser. No. 14/192,014, filed Feb. 27, 2014, which is a continuation claiming the benefit of and priority to U.S. patent application Ser. No. 13/191,893, filed Jul. 27, 2011, now issued as U.S. Pat. No. 8,690,913, which is a continuation claiming the benefit of and priority to U.S. patent application Ser. No. 12/838,706, filed on Jul. 19, 2010, now issued as U.S. Pat. No. 8,016,858, which is a continuation claiming the benefit of and priority to U.S. patent application Ser. No. 11/488,369, filed Jul. 17, 2006, now issued as U.S. Pat. No. 7,758,613, which is a continuation claiming the benefit of and priority to U.S. patent application Ser. No. 10/761,491, filed Jan. 20, 2004, now issued as U.S. Pat. No. 7,077,856, which is a divisional claiming the benefit of and priority to U.S. patent application Ser. No. 09/510,927, filed Feb. 22, 2000, now issued as U.S. Pat. No. 6,716,233, which is a continuation-in-part claiming the benefit of and priority to U.S. patent application Ser. No. 09/324,452, filed Jun. 2, 1999, now issued as U.S. Pat. No. 6,443,973, the disclosures of which are hereby fully incorporated by reference.

FIELD OF THE INVENTION

The present invention relates generally to a medical tool comprising an electromechanical driver which transmits information to and receives information from, and thereby controls, a surgical instrument attachment, and more specifically to the mechanisms employed to provide such remote direction and information relaying between said electromechanical driver and said surgical instrument attachment.

BACKGROUND

It shall be understood at the outset, that the present invention has many applications within the field of surgery. This disclosure shall not, therefore, be read as limiting of the scope of the invention by the specific medical or surgical applications which may be described herein, as they are only used as elucidating examples of such applications in which the present invention may be employed to enhance the outcomes and/or surgical efficiency. In particular, the present disclosure is directed to embodiments used in colon surgery, and specifically to anastomosing, resecting, and stapling instruments, however, the same invention may be applied to other surgical applications in the fields of gynecological surgery, cardiovascular surgery, and general surgery.

Upon identification of cancerous or other anomalous tissue in the gastrointestinal tract, surgical intervention is often prescribed. The field of cancer surgery, and more specifically, the surgical procedure by which a section of the gastrointestinal tract which includes cancerous or anomalous tissue is resected, includes a number of uniquely designed instruments. In combination with a description of the present instrumentation and their functions, a description of the state of the art in this surgical procedure shall also be provided.

The first question which must be answered when determining how to treat gastrointestinal cancer relates to the specific location of the cancerous tissue. This is very important insofar as the instruments which are provided in the present art have limitations relating to how far they may be inserted into the gastrointestinal tract. If the cancerous tissue is too far up the colon, for example, then the standard instrumentation provided is unusable, thus requiring special accommodations. These accommodations generally increase the risk of contamination of the surrounding tissues with bowel contents, increase the length of the surgery and the corresponding need for anesthesia, and eliminate the benefits of precise anastomosing and stapling which comes from utilizing a mechanized device.

More specifically, in the event that the cancerous tissue is located at a position in the colon which is accessible by the present instrumentation, the patient's abdomen is initially opened to expose the bowel. The surgeon then utilizes a linear cutter and stapling device which cuts the tube of the colon on either side of the cancerous tissue, thereby creating two stapled ends of the bowel (a distal end which is directed toward the anus, and the proximal end which is closest to the small intestine). This is done in order to temporarily minimize contamination.

The surgeon then partially opens the proximal end and inserts the removable anvil portion of an anastomosing and stapling instrument into the exposed proximal end. This step, as well as those of the remainder of the surgical procedure, are related to the functioning of this surgical instrument. More particularly, and with respect to FIG. 1, the surgeon begins by taking the instrument 30 and manually turning the dial 32 at the base of the handle 34 which causes the anvil head 36 at the opposite end to advance forward. The surgeon continues to turn the dial 32 until the anvil head 36 advances to its most extreme extended position. This manual turning requires nearly thirty full rotations. Once fully extended, the anvil head of the instrument is decoupled therefrom and is inserted into the partial opening of the proximal end such that the coupling post extends outwardly therethrough. This partial opening of the proximal end is then sutured closed. The extending shaft 38 of the anastomosing and stapling instrument 30 is then inserted and advanced into the lower colon, transanally, until the coupling stem 40 thereof extends through the stapled distal end. The surgeon then joins the coupling ends of the anvil and shaft together and begins to manually rotate the dial in the handle again, this time bringing the anvil head closer to the end 42 of the shaft.

Once the anvil head and shaft are brought close together, after the surgeon has manually rotated the dial another thirty times, a grip-style trigger 44 in the handle is manually actuated. This actuation causes a circular blade 46 to advance axially out from the tip of the shaft, and into contact with the opposing face 48 of the anvil 36. The blade cuts through the stapled-closed ends of the proximal and distal ends of the colon, thereby also cutting a new pair of ends of the proximal and distal portions of the colon. The tissue which has been severed is held in an interior volume at the end of the shaft.

In lock step with the cutting, the freshly opened ends are joined together by a series of staples 50 which are advanced through holes in the perimeter of the tip of the shaft (being pressed against and closed by the opposing face of the anvil). The coupled shaft and anvil are then withdrawn from the patient.

As with many such devices of the prior art, all of these devices are considered fully disposable, and are, in fact, thrown away after a single use. They are complicated devices, having multiple moving parts, requiring substantial structural integrity and, therefore, expense in manufacturing. The fact that they are used only once, and that no part can be used again, render the use of such devices expensive and wasteful of resources.

In addition to this failure, as can be readily observed from the preceding descriptions, the prior art devices suffer from numerous other limitations which would be desirable to overcome. These include the rigid and limited length shaft of the anastomosing and stapling instrument (which limits the portion of the gastrointestinal tract which may be treated by such a device), as well as the requirement that the surgeon manually actuate a number of different functions (including those associated with the dial and trigger of the anastomosing and stapling instrument and the multiple triggers of the cutting and stapling instrument).

Therefore, it has been a principal object of recent inventions to provide an instrument for cutting, anastomosing, and stapling, for use in gastrointestinal surgery, which reduces the waste of resources by permitting the reuse of portions thereof, can extend farther into the colon, and which are more simple to manipulate.

A substantial advance in the field of colon surgery has been disclosed in U.S. patent application Ser. No. 09/324, 452, entitled "An Electromechanical Driver Device for use with Anastomosing, Stapling, and Resecting Instruments", now issued as U.S. Pat. No. 6,443,973, which was invented by the same inventor as the present application, was assigned to the same assignee as the present invention, and the specification of which is hereby incorporated fully by reference.

In particular, this prior invention, made by the present inventor comprises an electromechanical driver assembly, mounted in a handle-shaped base unit, which couples to and motivates remote surgical attachments through a flexible shaft which may also be remotely manipulated by means of a series of steering wires which are controlled within the handle as well.

First, with respect to the handle component and the flexible shaft. The handle has a pistol grip-styled design, having one or more, and preferably two, finger triggers which are independently coupled to at least one, and preferably two separate motors which each turn separate flexible drive shafts (described more fully, hereinbelow). The motors are each dual direction motors, and are coupled to a manual drive switch mounted to the top of the handle, by which the user can selectively alter the turning direction of each motor. In addition to the motor components, the handle further includes several other features, including: (1) an remote status indicator; (2) a shaft steering means; and (3) at least one additional electrical supply.

The flexible shaft comprises a tubular sheath, preferably formed of a simple elastomeric material which is tissue compatible and which is sterilizable (i.e., is sufficiently rugged to withstand an autoclave). Within the elastomeric sheath are a pair of smaller fixed tubes which each contain a flexible drive shaft which is capable of rotating within the tube. The flexible drive shaft, itself, simply must be capable of translating a torque from the motor in the handle to the distal end of the shaft, while still being flexible enough to be bent, angled, curved, etc. as the surgeon deems necessary to "snake" through the colon of the patient. As suggested above, in conjunction with the manually actuatable steering means mounted to the handle, the sheath further includes at least two sets of steering wires which are flexible, but are coupled to the inner surface of the sheath near the distal end thereof. The steering wires may be axially translated relative to one another by actuation of the steering means, which action causes the sheath to bend and curve accordingly.

Referring now to one possible surgical instrument attachment which was disclosed as a preferred embodiment in the above referenced co-pending application entitled "An Electromechanical Driver Device for use with Anastomosing, Stapling, and Resecting Instruments", the anastomosing and stapling attachment, this attachment comprises an anvil portion, and a staple, blade and reservoir portion, which includes a pair of turning drive shafts which are coupleable to the drive components of the shaft element described above, and a corresponding pair of advancing and retracting nuts mounted to the turning drive shafts, but which are prevented from rotating and therefore linearly advance and retract along the shafts when they turn.

The anvil portion is bullet shaped, having a blunt nosed top portion, a flat cutting support surface on the bottom, and a freely rotating coupling post extending axially from the bottom surface. This coupling post is designed to be selectively coupleable and removable from the corresponding nut mounted to one of the turning drive shafts.

The staple, blade, and reservoir portion (SBR portion) is cylindrical in shape, forming a housing which has a hollow interior. It is this hollow interior which forms the reservoir. On the axially outward facing surface of the cylindrical wall of the housing are a series of staple ports, through which the staples of the device are discharged. A series of staple drivers are mounted within the cylindrical walls, beneath the staple ports, for driving the staples therethrough. The blade is similarly cylindrical, and seats in the inside of the housing, against the inner surface of the wall thereof. Both the blade and the staple driver are mounted to the second nut, which is, in turn, mounted to the other turning drive shaft. As the tuning drive shaft rotates, the nut (which is constrained against rotating) advances along the shaft, thus linearly advancing the blade and staple driver. The blade and the staple driver are, therefore, selectively advanceable axially outward from the housing, in accordance with actuation of the appropriate trigger on the handle.

In a preferred embodiment set forth in the referenced application, the anvil portion and the SBR portion further comprise an electromagnetic sensor mechanism, coupled to the LCD indicator of the handle, which sensor is activated when the two portions have approached each other to the extent necessary for a safe staple firing, whereby the surgeon may have remote knowledge of the state of the attachment disposed within the colon.

An observed problem with prior art devices used in the anastomosing, stapling and resecting surgical procedure described above, relates to the best indications which the surgeon may remotely receive as to the conditions within the patients colon. For example, it is critical that the surgeon know whether the tissue being coupled forms a contiguous and sealed ring, such that the recoupled ends of the colon do not contain a hole through which bowel contents may leak into the body cavity. Post surgical infection rates due to such failures are a leading cause of complications and are often severe and are a leading cause of morbidity.

An associated issue of which surgeons who carry out these procedures must be cognizant relates to the ongoing viability of the tissue which has been resealed. A frequent post-surgical problem relates to the tissue necrosis which may occur if the staple ring is too tightly compressing the tissue, and preventing necessary blood flow thereto. A simple light-based mechanically measured distance indicator means is insufficient to avoid both of these problem. Prior art devices fail to provide the means by which information regarding the state of the tissue being manipulated may be measured and used by the surgeon, and the instrument itself, to ensure a more positive outcome.

It shall be understood that this problem, i.e., the failure of remotely controlled surgical instruments to provide for the gathering, displaying, and influencing of automatic actions, of information critical to the success of the surgical procedure simultaneously with the action of the device, is not limited to the specific instances discussed above. Rather, this failure is prevalent throughout surgical instrumentation.

It is therefore a principle object of the present invention to provide a surgical attachment which is remotely controlled and includes information-gathering sensors, communication and processing capacities, information storage capacity, and indicating means by which the user and/or remote decision-making systems may choose to control the instrument and activate the features of the attachment in accordance with the gathered and relayed information.

Other objects of the present invention shall be recognized in accordance with the description thereof provided hereinbelow, and in the Detailed Description of Preferred Embodiments in conjunction with the remaining Figures.

SUMMARY OF THE INVENTION

The preceding objects of the invention are provided by an electromechanical driver, a flexible shaft, and remote surgical attachment including a controller processor unit mounted in the handle which is connected via cabling in the flexible shaft to a sensor and memory unit in the remote attachment. More particularly, with respect to the bowel surgery anastomosing, resecting, and stapling attachment described above in the Description of the Prior Art, the present invention shall be set forth with respect to the same application. Specifically, with respect to the sensor and memory unit mounted in the anastomosing, resecting, and stapling attachment, the sensor utilized is a pulse oximeter.

First, as described above, the present invention is preferably embodied as a subsystem of a device which comprises three components, which are (1) an electromechanical driver, (2) a flexible shaft, and (3) an anastomosing, resecting, and stapling attachment.

First, with regard to the electromechanical driver, the handle has a pistol grip styled design, having at least two finger-actuatable triggers which independently initiate motors which turn drive shafts mounted within the flexible shaft. The handle further includes a remote status indicator coupled to the processor unit in the handle. This indicator provides either visual, audio, or electrical output (to be output to a separate display device). The handle and flexible shaft further include a shaft steering means comprised of steering wires controlled by a handle mounted motor drive system including a manually actuatable steering means for directing the steering means, for example, a joystick or trackball, described more fully in co-pending U.S. patent application U.S. Ser. No. 09/510,923, now issued as U.S. Pat. No. 6,517,565, entitled "A Carriage Assembly for Controlling a Steering Wire Steering Mechanism within a Flexible Shaft", which has been assigned to the same assignee as the present invention, and which is incorporated herein fully by reference.

In this embodiment of the electromechanical driver, the driver components are integrated with the controller components. It should be noted that other embodiments of the electromechanical driver may comprise a driver unit which is physically separate from a controller unit. That is, the driver unit may comprise the above-described motors and the above-described steering means, and the controller unit may comprise the above-described triggers, the above-described remote status indicator, as well as the above-described manually actuatable steering means. The controller unit components communicate with the driver unit components by wireless transmission, for example, through infrared, radio waves, other electromagnetic waves, or ultrasound. In such a configuration, for example, the driver unit may be located out of the surgeon's arm's reach, while the controller unit may be selectively coupleable to that portion of the flexible shaft which is closer to the patient and closer to the surgeon. It should be further understood that additional embodiments of the electromechanical driver assembly may comprise more than two separate units, and such units may each house only one, or more than one, of the above-described separate components, all communicating by wireless means as described above. For example, the remote status indicator described above could be part of a third unit which mounts to a visor wearable by the surgeon. It should be further understood that all communications between these components as described herein may in such alternative embodiments take place by wireless means.

Second, with respect to the flexible shaft, the shaft comprises a tubular sheath, preferably formed of a simple elastomeric material which is tissue compatible and which is sterilizable (i.e., is sufficiently rugged to withstand an autoclave). Within the elastomeric sheath are a pair of smaller fixed tubes, each of which contain a flexible drive shaft which is capable of rotating within the tube. As suggested above, in conjunction with the steering means mounted in the handle, the sheath further includes at least two steering wires which are flexible, but are coupled to the inner surface of the sheath near the distal end thereof. In addition, the flexible shaft includes a least one electrical lead and corresponding coupling terminals at each end, for coupling to the processor and controller means in the handle with the sensor and memory components in the distally mounted surgical attachment.

Third, with regard to the anastomosing, resecting, and stapling attachment, a single example of the many alternative surgical attachments which may include aspects of the present invention is now described. This attachment comprises a selectively advanceable and retractable anvil portion, and a staple, blade, sensor, and reservoir portion. This latter element includes the drive elements necessary to move the anvil forward and back, as well as the motive elements which drive the staples and blade through the tissue. These motive elements are coupleable to the drive components of the shaft element described above. Included in the staple, blade, sensor and reservoir portion, also, are a pulse oximeter sensor and a tissue proximity sensor, as well as a memory unit which contains important identification information which may be retrieved by the processor unit in the handle upon connection to the flexible shaft.

As stated above, when initially coupled to the flexible shaft (which shall be hereinafter taken to be permanently coupled to the handle unit), and the handle is powered up, the first internal act to take place is for the processor unit in the handle to query the memory unit in the attachment as to its identity and status. More particularly, as the anastomosing, resecting, and stapling attachments may come in different diameters, shapes, lengths, and stapling arrangement (as well as many other potential variations) which are readily readable by the handle mounted processor unit and displayed for the user either on a remote display panel to which the handle is coupled, or on a display screen which is integrally included in the handle itself.

The status of the attachment shall also be queried, for example, as to what the functionality of the attachment is, and whether or not it has been previously used, and therefore, no longer capable of firing a second time.

Once this information has been gathered, and it is determined that the attachment is the appropriate one, the surgical step for which this attachment is utilized may continue. In particular, the anvil tip is advanced via action of the drive motor and drive elements of the handle, shaft, and attachment, until it may be manually separated from the remainder of the attachment. The appropriate opening is made in the previously cut and stapled closed proximal end of the bowel and the anvil tip of the attachment is placed therein. The remainder of the attachment and the appropriate length of the flexible shaft is inserted through the rectum and up the bowel until the attachment coupling shaft is advanced through a small opening in the cut and stapled closed distal end of the bowel section.

After recoupling, the anvil portion is retracted toward the stapling portion until it is mechanically determined that the two portions are within the range which is appropriate for staple firing. At this time, the physician user is unable to simply remotely fire the staples. This lock out feature is maintained by the processor unit until such time as the surgeon causes the processor until in the handle to query the tissue proximity sensor and the pulse oximeter sensor in the attachment to determine if the tissues to be stapled together form a completely contiguous ring so that the two tubular sections of bowel can be properly mechanically united. This measurement may be made optically, or by any other suitable means, by which the transmission of some signal which should be blocked by the intervening tissue is received by an opposing sensor. The results of this query are then relayed back to the processor in the handle which carries out the appropriate analysis. If the proximity query results in a negative analysis outcome, an indicator light, audible alarm, or other suitable means of alerting the surgeon to this condition is provided. The processor will also disarm the stapling mechanism (by removing power to the drive mechanisms, for example) to prevent an attempted override by the surgeon.

If the proximity query results in a positive response, however, the next in the series of tests to determine if the surgeon may safely join the sections of bowel is carried out. Specifically, the processor in the handle activates the pulse oximeter sensor and queries it regarding whether the proper level of blood profusion remain in the tissue sections to be joined. As suggested above, if the stapling procedure has the effect of cutting off the necessary blood supply to sections of the joined tissue, a necrotic region will develop in the bowel, and future complications (which may be fatal) will arise. The results of this query are also relayed to the processor in the handle. Again, if the results of the processing of this information is negative, an indication of this state is provided by the processor. As above, if negative, the surgeon will be unable to mechanically fire the staples, as the processor will disarm the motor assembly.

Additional features and aspects of the present invention are set forth in greater detail in the description of the preferred embodiments provided hereinbelow.

A BRIEF DESCRIPTION OF THE DRAWINGS

A DETAILED DESCRIPTION OF THE PREFERRED EMBODIMENTS

While the present invention will be described more fully hereinafter with reference to the accompanying drawings, in which particular embodiments are shown, and with respect to methods of surgical use, it is to be understood at the outset that persons skilled in the art may modify the invention herein described while achieving the functions and results of this invention. Accordingly, the descriptions which follow are to be understood as illustrative and exemplary of specific structures, aspects and features within the broad scope of the present invention and not as limiting of such broad scope. Like numbers refer to similar features of like elements throughout.

Figure 1:
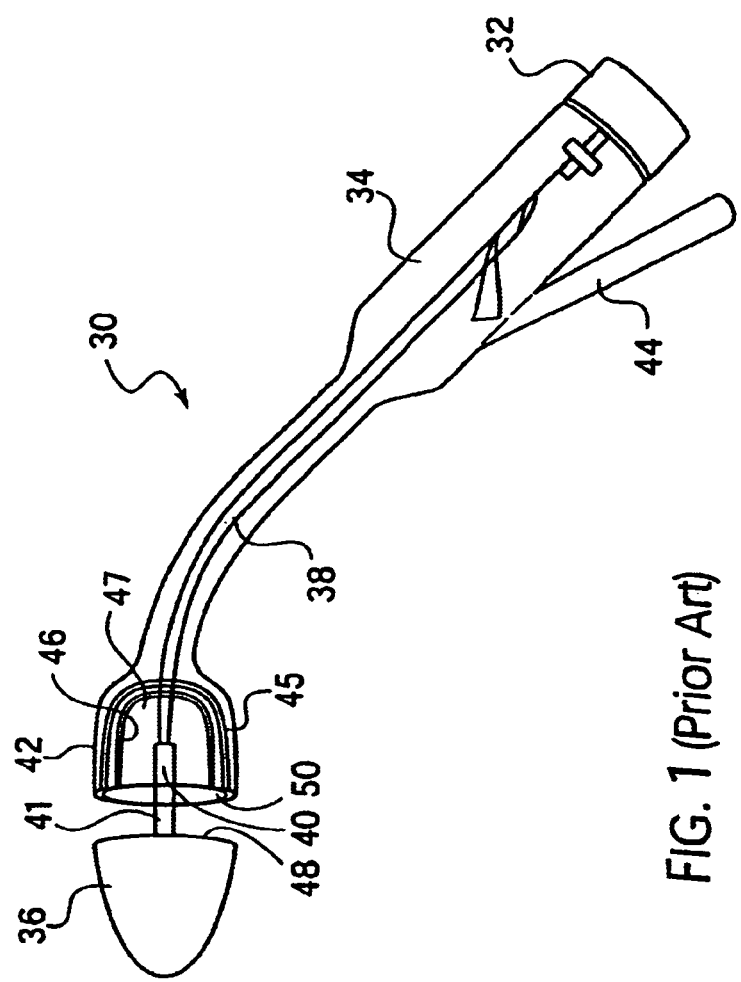
FIG. 1 is a side perspective view of an anastomosing, resecting, and stapling instrument of the prior art.
Figure 2:
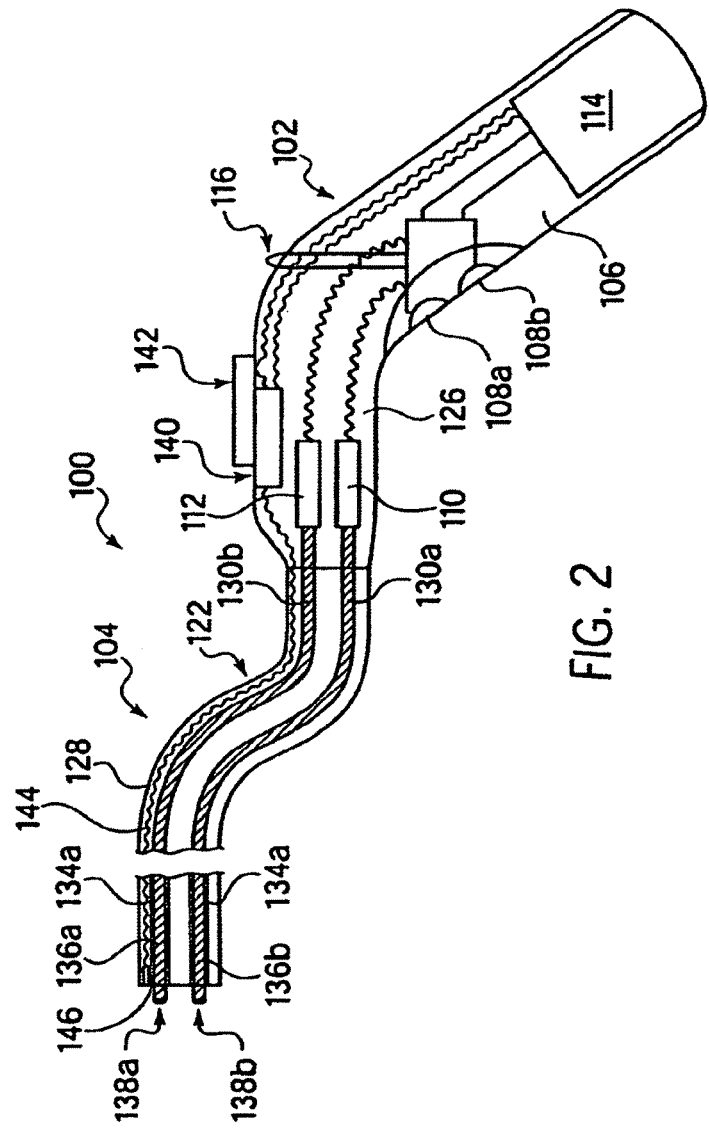
FIG. 2 is a side cross-section view of a handle and flexible shaft of the present invention, wherein important internal features of the control systems are provided in detail.

Referring now to FIG. 2, with respect to the electromechanical driver 100, the driver has a handle portion 102 and a flexible drive shaft portion 104. The handle 102 includes a portion which is shaped in a manner which is easily gripped by the surgeon operator, for example, in the embodiment provided herein the handle comprises a pistol grip-styled portion 106. The grip portion 106 includes at least two, and in the present embodiment exactly two, independently finger-actuateable triggers 108a,108b. The finger triggers 108a,108b are independently coupled to separate motors 110,112, housed within the interior volume of the handle 100. Each motor 110,112 turns a separate flexible drive shaft (described more fully, hereinbelow).

More particularly, with respect to the motors 110,112, each is a dual direction motor. In addition to being coupled to the finger-actuateable switch, the motors are also each separately coupled to a power source 114 (which is a common source in the present embodiment) and a manual drive switch 116. The manual drive switch 116 is provided on the top of the handle 100, such that the surgeon operator can selectively alter the turning direction of each motor. In the preferred embodiment, the power source 114 supplying the motors 110,112 is a single direct current supplying removable and rechargeable battery pack. It shall be understood that alternative power sources, including dual direct current sources or single remote alternating current sources (such as the alternating current provided from standard United States 120 Volt, 60 Hertz wall outlets) may be used in conjunction with alternative embodiments. In the event that the driver device should be useable with an alternating current, either a transformer can be included between the motor and the power source, or a more sophisticated intermediate gearing assembly may be provided between the motor and the extended turning drive shaft.

In addition to the motors 110,112 components and the related power and drive switch elements, the handle 100 further includes a motor driven shaft steering carriage assembly, which is coupled to a manual input means, which is coupled to steering wires in the flexible shaft for selectively steering the distal tip of the flexible drive shaft 122.

The handle also includes a processor element 140 and output display device 142 (mounted on the exterior of the handle). The processor element 140 and the display device 142 are each electrically coupled to the power source to provide electrical power to carry out their actions. The processor unit and display element are similarly coupled to one another to permit the processor to display the signal output generated thereby. The processor unit is also coupled via an electrical cable 144 to an input terminal 146 at the distal tip of the flexible shaft 122.

More particularly, with respect to the flexible shaft 122, the shaft comprises a tubular sheath 128 which is formed of a simple, tissue compatible, elastomeric material. As this device is to be reused, it is important that the material be sterilizable (i.e., is sufficiently rugged to withstand an autoclave). While the embodiment illustrated comprises a contiguous handle 100 and shaft 122, it shall be understood that one having ordinary skill in the art may provide an alternative embodiment having a separable handle and shaft, thus permitting alternative shaft lengths for alternative purposes. In such cases, the flexible shaft 122 and the handle 100 portions should include an interface between the proximal end of the shaft and the distal end of the handle which should include a coupling means for the drive components.

Specifically regarding the drive components 130a,130b of the shaft 122, within the elastomeric sheath 128 are a pair of smaller fixed tubes 134a,134b which each contain a flexible drive shaft 136a,136b which is capable of rotating within the corresponding tube 134a,134b. The flexible drive shaft 122, itself, simply must be capable of translating a torque from the motor in the handle to the distal end 138a,138b of the shaft 122, while still being flexible enough to be bent, angled, curved, etc. as the surgeon deems necessary to "snake" through the colon of the patient. For example, the drive shafts may comprise a woven steel fiber cable, a high tensile strength polymeric material, or a sufficiently flexible unitary metal shaft.

In order for the distal ends 138a,138b of the drive shafts 136a,136b to couple with an attachment, such as anastomosing, resecting, sensing, and stapling attachment, the distal tips 138a,138b of the drive shafts must have a conformation which permits the continued translation of torque. In the present embodiment, this coupling is achieved by a geometric fitting, and more precisely, the distal tips of the drive shafts are hexagonal, and thereby fit into a hexagonal recesses in the coupling interface of the attachment. In a preferred embodiment, the attachment and the distal end of the shaft should include a collar, or other aligning means, for facilitating the fitting of the attachment onto the distal end of the shaft.

In addition, the shaft includes an electrical wire 144 extending from the end coupled to the handle to the end which couples to the surgical attachment. The first end of the shaft includes the terminal inputs which are coupled to the processor unit. The second end includes a terminal 146 for coupling to the corresponding electrical input/output of the surgical attachment (described more fully hereinbelow).

Figure 3:
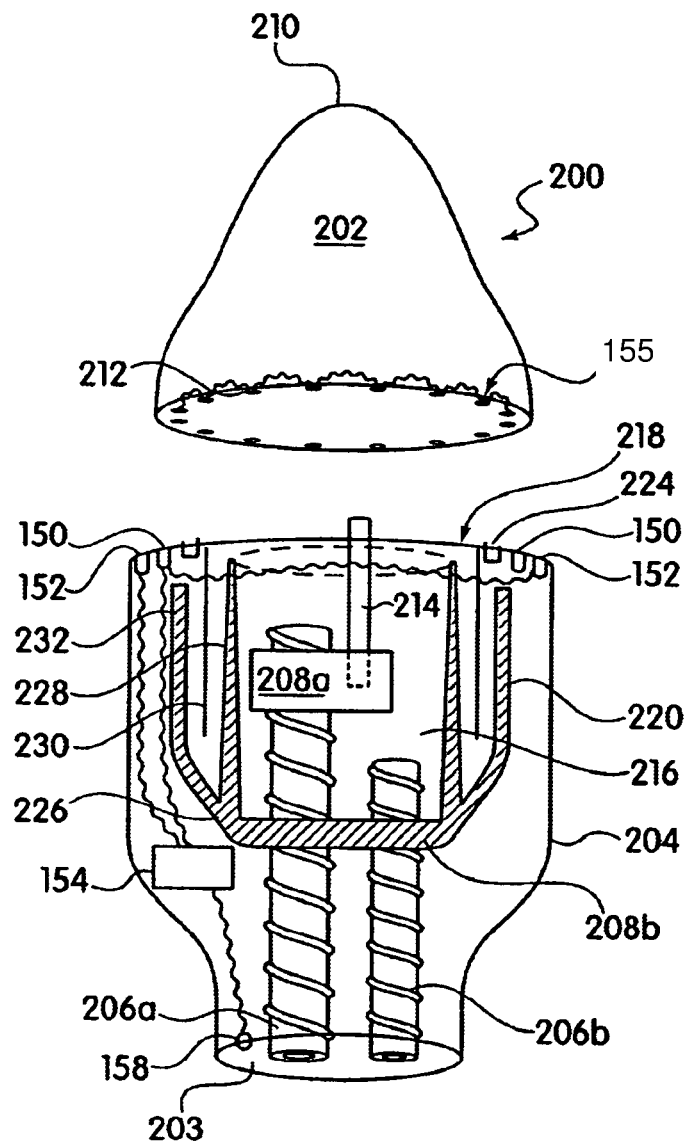
FIG. 3 is a side cut-away view of an anastomosing, resecting, sensing, and stapling attachment which is also an aspect of the present invention.

With reference now to FIG. 3, a preferred embodiment of the anastomosing and stapling attachment 200 is described. This attachment comprises an anvil portion 202, and a staple, blade, sensor, and reservoir (SBSR) portion 204, which includes a pair of turning drive shafts 206a, 206b which are coupleable to the drive components 136a, 136b of the driver component described above with reference to FIG. 2, and a corresponding pair of advancing and retracting members 208a, 208b mounted within tracks and to the turning drive shafts, which are thereby prevented from rotating and therefore linearly advance and retract along the shafts 206a, 206b when they turn. The anvil portion includes a series of light detectors. The SBSR includes pulse oximeter and tissue proximity sensors 150, 152 and a memory and signal transmitter and receiver member 155 which couples to the flexible shaft at the corresponding terminal thereon by way of an electrical coupler 158 shown.

The anvil portion 202 is bullet shaped, having a blunt nosed top portion 210, a flat cutting support surface 212 on the bottom, and a coupling post 214 extending axially from the bottom surface. This coupling post 214 mounts to the first advancing and retracting member 208a which is mounted within a linear track whereby rotation of the shaft 206a causes the member 208a and the anvil 202 coupled thereto to move axially, but not rotationally. The exterior surface of the face of the anvil which opposes the SBSR includes a series of light emitting diodes 154.

The staple, blade, sensor, and reservoir portion (SBSR) portion 204 is cylindrical in shape, forming a housing which has a hollow interior 216. It is this hollow interior which forms the reservoir. On the axially outward facing surface 218 of the cylindrical wall 220 of the housing are a series of staple ports, through which the staples 224 of the device are discharged. A unitary blade and cylindrical staple driver component 226 is seated within the housing. A circumferential pulse oximeter 150 is mounted in the housing on the outside rim of the housing, radially adjacent to the staple ports. A pulse oximeter is a simple device which shines a specific frequency of light through a section of tissue to measure the absorption rate of the light. Because oxygenated blood has a different color than does blood which is not fully oxygenated, the profusion of fresh blood through a tissue may be determined by this device. Therefore, the pulse oximeter comprises a series of light emitting elements 154 on the anvil and light sensors 150 mounted around the circumferential rim of the housing member. As shown, the components of the pulse oximeter are electrically connected via wires running through the coupling post of the anvil.

In addition, the attachment also includes a tissue proximity sensor 152, a portion of which is similarly mounted to the external rim of the housing, radially adjacent to the pulse oximeter 150 and the staple ports. In addition, the tissue proximity detector 152 comprises a series of simple light emitting elements 154 on the anvil (for example the same light emitting elements of the pulse oximeter), and a corresponding series of light detectors 152 mounted around the circumferential rim of the housing member. In the proximity sensor, if the tissue which is supposed to be disposed between the anvil and housing is present, then the proximity sensor's light detectors will not receive a signal (or at least below a set threshold), alternatively, if the tissue is missing, then the light detectors will receive a stronger signal, indicating that there is no tissue blocking the transmission of the light.

More particularly, the blade and staple driver component comprises a single element having two concentric cylindrical portions. The blade portion 228 seats within the hollow interior 216, against the interior wall 230 thereof. The staple driver portion 232 seats within the wall 230 of the SBSR portion and includes a series of outwardly projecting protuberances which push against staples mounted within the staple ports.

The blade 228 and staple driver portions 232 are coupled at the interior end thereof to a threaded member 208b which seats around turning shaft 206b. The threaded member 208b is constrained within a linear track so that the blade and staple driver are advanced linearly upon rotation of the turning shaft 206*b*.

Figure 4:
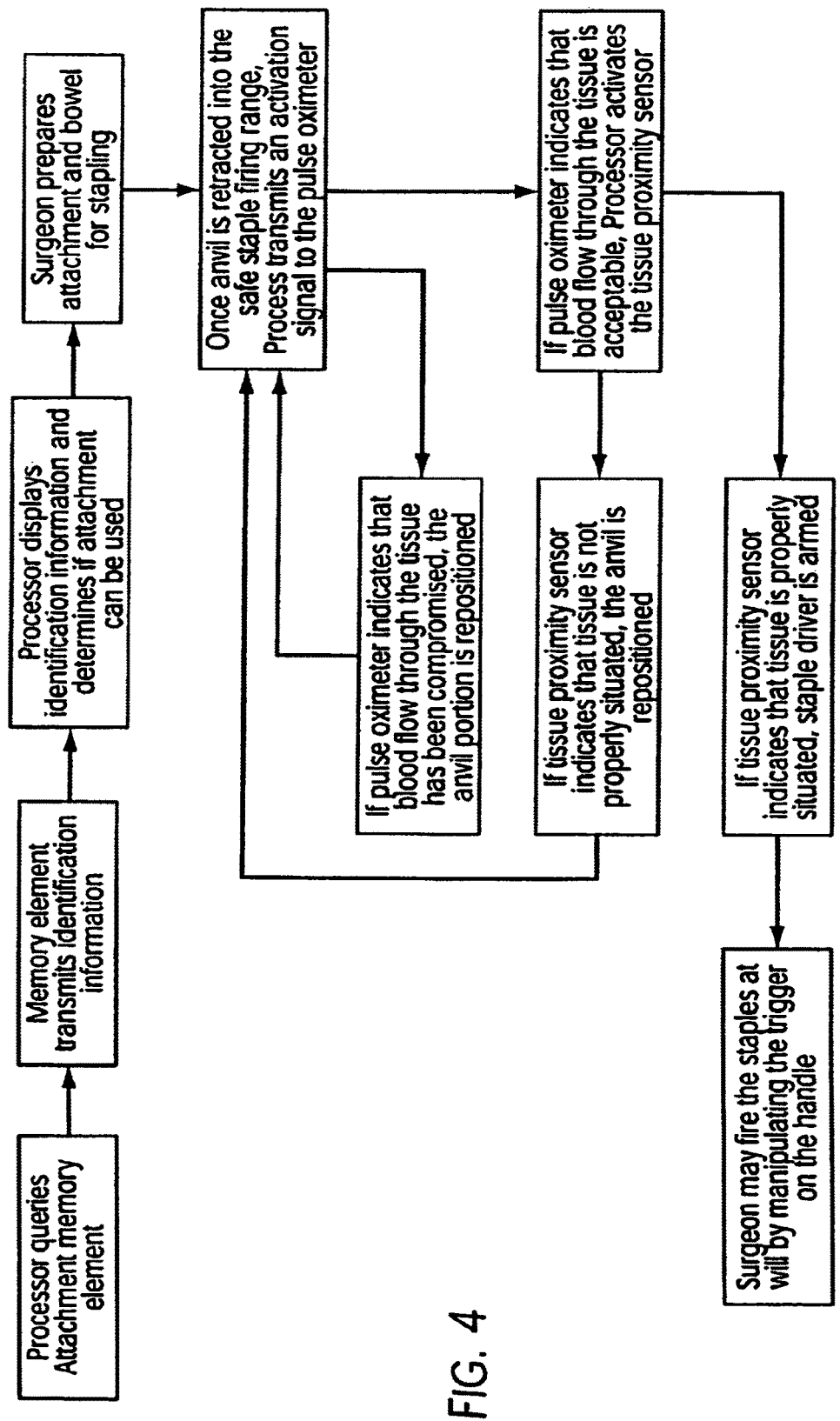
FIG. 4 is a flow chart illustrating the logical sequence of processor, sensor, and mechanical actions which are illustrative of features of the present invention.

In practice and with reference to the flow chart provided in FIG. 4, this attachment and the associated controller features of the present invention are utilized once the section of the colon to be removed has been resected and the two opposing ends of the adjacent bowel have been stapled shut. The surgeon begins by coupling the anastomosing, resecting, sensing, and stapling attachment 200 to the distal end of the flexible shaft. The processor in the handle unit queries the memory element in the attachment and requests identification information. The attachment transmits the requested information, including size, status and functionality information. The processor in the handle outputs this information to the display panel, for visual inspection by the surgeon user. The processor further establishes whether the surgeon may activate the driver means in correspondence to whether the information received from the attachment was acceptable (i.e., is it unused and functional).

In the event that the identification information received is acceptable, the surgeon then triggers the electromechanical driver to advance the anvil portion 202 to its fullest extent. The anvil head 202 is then decoupled from the first advancing and retracting member 208 and inserted into the stapled proximal end of the bowel (which is then opened partially to receive the anvil head). The proximal end of the bowel is then sutured closed. The surgeon then advances the shaft 206*a* and the SBSR portion 204 of the attachment up the colon until it extends through the stapled distal end of the colon. (Alternatively, the surgeon may advance only the flexible shaft up the colon and then reattach the SBSR portion to the distal end once it emerges from the distal end of the bowel.) The surgeon then couples the anvil 202 to the advancing and retracting member 208*a* by rotation of the corresponding drive shaft 136*a*. Subsequent reverse biasing and triggering of the same motor in the handle 100 causes the anvil 202 to retract toward the SBSR portion 204.

Once retracted into the safe staple firing range, the processor disables the staple firing motor and again queries the attachment. In fact, the processor in the handle transmits an activation signal to the pulse oximeter, to sense the blood profusion through the tissue compressed between the anvil and SBSR portions. If the response received from the sensor is that the blood flow through the tissue has been compromised, the anvil portion is repositioned and the process begins anew. If the response received from the sensor is that the blood flow is acceptable, then the processor activates the tissue proximity sensor. If the response is that the tissue is properly situated, then the staple driver is armed and the surgeon can fire the staples at will by manipulating the trigger on the handle. If the proximity detector response is negative, the anvil is repositioned.

While there has been described and illustrated new and novel electromagnetic driver mechanisms having an attachment processor controller, for use with surgical attachments, it will be apparent to those skilled in the art that variations and modifications are possible without deviating from the broad spirit and principle of the present invention which shall be limited solely by the scope of the claims appended hereto.

What is claimed is:

1. A surgical system, comprising:
   a handheld electromechanical driver, including:
      a handle portion;
      at least one motor supported in the handle portion; and
      a processor in communication with the at least one motor; and
   a surgical attachment, selectively coupleable to the handheld electromechanical driver, including:
      an anvil portion;
      a staple, blade, sensor, and reservoir (SBSR) portion coupleable to the anvil portion; and
      a memory unit included within the SBSR portion configured to store identity information and status information of the surgical attachment,
   wherein, when the surgical attachment is coupled to the handheld electromechanical driver, the processor of the handheld electromechanical driver queries the memory unit of the surgical attachment regarding the identity information and status information.

2. The surgical system according to claim 1, wherein the surgical attachment is an interchangeable surgical attachment.

3. The surgical system according to claim 1, wherein the surgical attachment is an anastomosing, resecting, and stapling attachment.

4. The surgical system according to claim 1, wherein the identity information includes at least one of size, diameter, shape, length, and stapling arrangement of the surgical attachment.

5. The surgical system according to claim 1, wherein the status information includes at least one of functionality and usage history of the surgical attachment.

6. The surgical system according to claim 1, wherein the SBSR portion includes drive elements for moving the anvil portion.

7. The surgical system according to claim 1, wherein the SBSR portion includes motive elements for driving a blade and staples through tissue.

8. The surgical system according to claim 1, wherein the identity information and the status information are displayed on a remote display coupled to the handle portion.

9. The surgical system according to claim 1, wherein the identity information and the status information are displayed on a display integrated on the handle portion.

10. The surgical system according to claim 1, wherein the processor establishes when the handheld electromechanical driver is activatable based on the identity information and the status information received.

11. A surgical attachment for use in a surgical system having an electromechanical driver including a processor, the surgical attachment including:
   an anvil portion;
   a staple, blade, sensor, and reservoir (SBSR) portion coupleable to the anvil portion; and
   a memory unit included within the SBSR portion configured to store identity information and status information of the surgical attachment,
   wherein, when the surgical attachment is coupled to the electromechanical driver, the processor queries the memory unit of the surgical attachment regarding the identity information and status information.

12. The surgical attachment according to claim 11, wherein the surgical attachment is an interchangeable anastomosing, resecting, and stapling attachment.

13. The surgical attachment according to claim 11, wherein the identity information includes at least one of size, diameter, shape, length, and stapling arrangement of the surgical attachment.

14. The surgical attachment according to claim 11, wherein the status information includes at least one of functionality and usage history of the surgical attachment.

15. The surgical attachment according to claim 11, wherein the SBSR portion includes drive elements for moving the anvil portion.

16. The surgical attachment according to claim 11, wherein the SBSR portion includes motive elements for driving a blade and staples through tissue.

17. The surgical attachment according to claim 11, wherein the identity information and the status information are displayed on a remote display coupled to a handle portion of the surgical system.

18. The surgical attachment according to claim 11, wherein the identity information and the status information are displayed on a display integrated on a handle portion of the surgical system.

19. The surgical attachment according to claim 11, wherein the processor establishes when the electromechanical driver is activatable based on the identity information and the status information received.

20. The surgical attachment according to claim 11, further comprising a sensor assembly, the processor of the electromechanical driver configured to receive data from the sensor assembly.

\* \* \* \* \*